United States Patent [19]

Thimsen et al.

[11] Patent Number: 4,649,919
[45] Date of Patent: Mar. 17, 1987

[54] SURGICAL INSTRUMENT

[75] Inventors: James A. Thimsen; Terry L. Whipple, both of Richmond; Richard B. Caspari, Maidens, all of Va.

[73] Assignee: Precision Surgical Instruments, Inc., Richmond, Va.

[21] Appl. No.: 694,012

[22] Filed: Jan. 23, 1985

[51] Int. Cl.⁴ .............................................. A61B 17/32
[52] U.S. Cl. ................... 128/305; 128/305.1; 604/22; 30/133; 30/240
[58] Field of Search ................ 128/305, 305.1, 303 R, 128/310, 751–755; 30/240, 133; 604/22

[56] References Cited

U.S. PATENT DOCUMENTS

| | | | |
|---|---|---|---|
| 3,732,858 | 5/1973 | Banko | 128/305 X |
| 3,945,375 | 3/1976 | Banko | 128/305 X |
| 4,067,340 | 1/1978 | Le Noir | 128/305 |
| 4,203,444 | 5/1980 | Bonnell et al. | 128/276 |
| 4,274,414 | 6/1981 | Johnson et al. | 128/305 |
| 4,368,734 | 1/1983 | Banko | 128/305 |
| 4,512,344 | 4/1985 | Barber | 128/305 |
| 4,517,977 | 5/1985 | Frost | 128/305 |

FOREIGN PATENT DOCUMENTS 2362157  11/1974  Fed. Rep. of Germany ...... 128/305

Primary Examiner—Michael H. Thaler
Attorney, Agent, or Firm—Richard P. Matthews

[57] ABSTRACT

A hand held surgical instrument for use in removing body tissue from a human body. It is particularly useful in arthroscopic surgery of joints such as of the knee or shoulder, but may also be used to remove tissue from the stomach, abdomen, jaw or other portions of the body. An auger-like helical cutter is motor driven at speeds in excess of 1,000 rpm within a stationary outer cylindrical sheath member. The helical cutter is ground to provide a generally concave distal end which gives it a generally fish-tailed appearance and the ability to cut endwise, i.e., to effect an axial boring cut. In addition, the cylindrical sheath member is provided with a pair of longitudinally extending, diametrically opposed tab members at its distal end. Each of the tabs has at least one longitudinally extending edge thereof ground to provide a cutting edge which co-acts with the auger-like cutter blade to sever body tissue insertable between the tabs.

6 Claims, 14 Drawing Figures

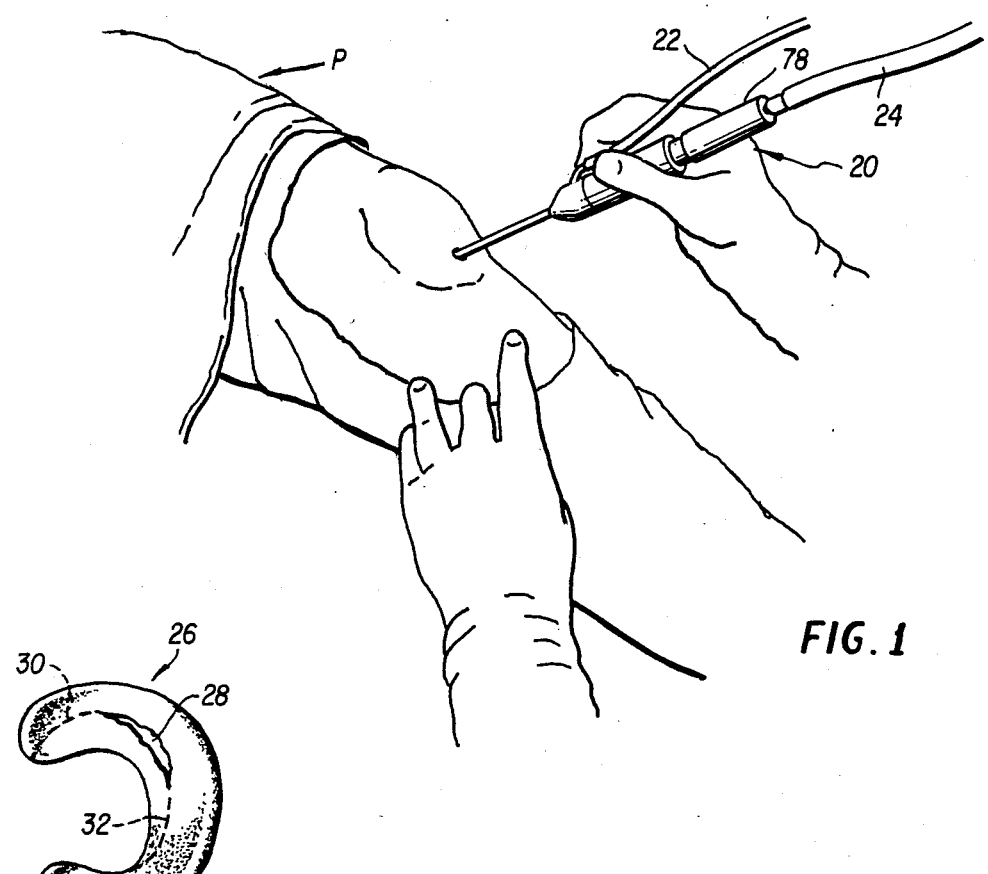
FIG. 1
FIG. 2
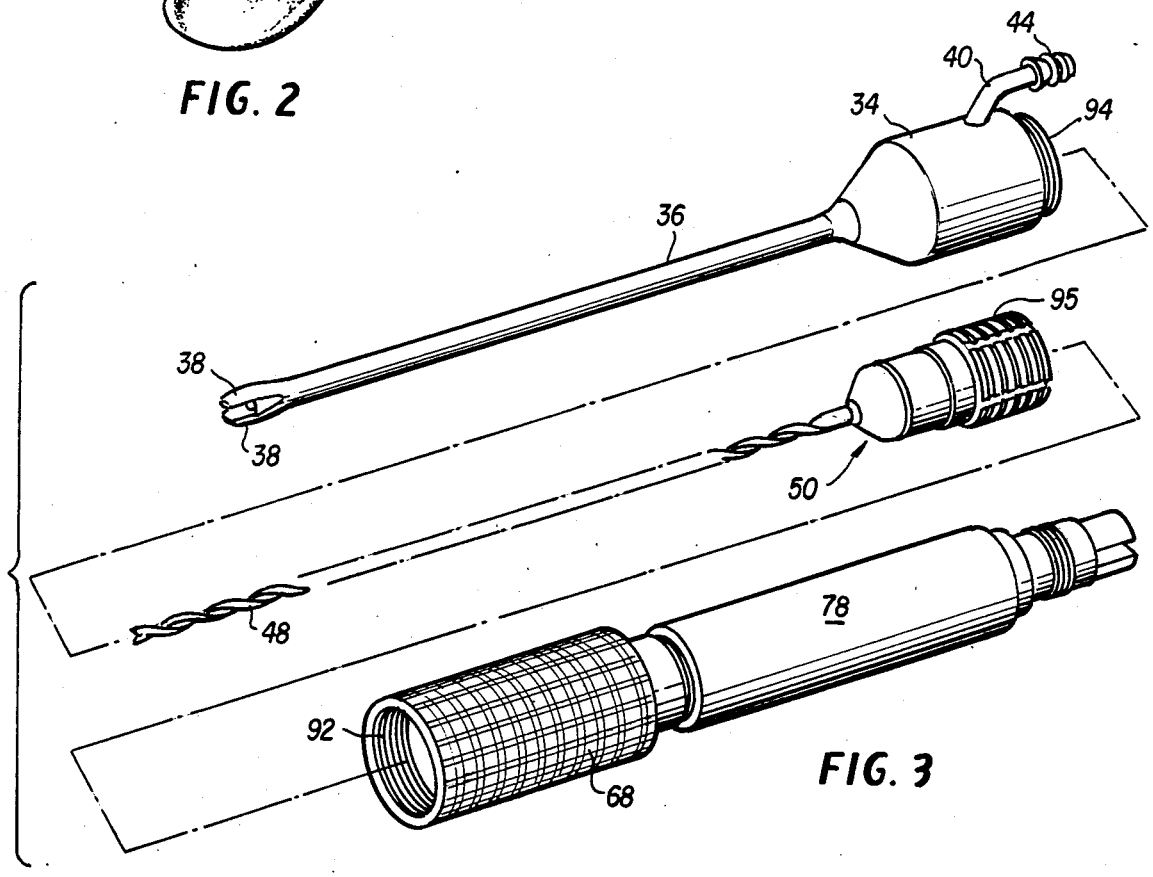
FIG. 3

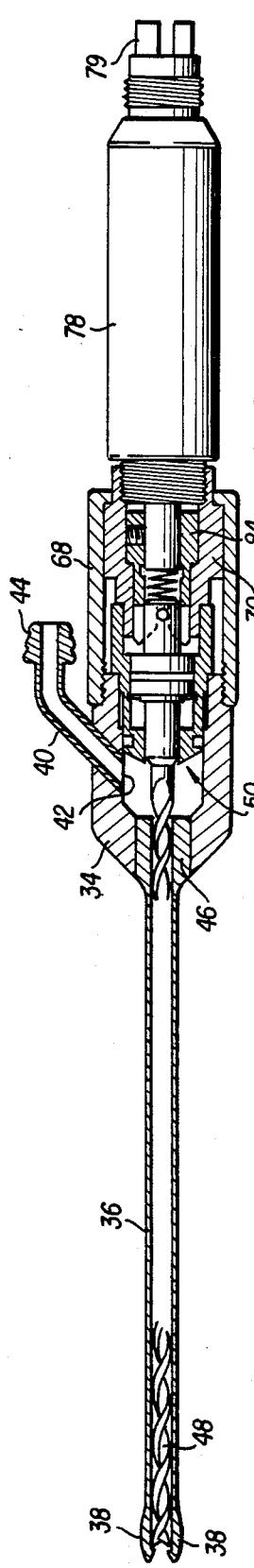
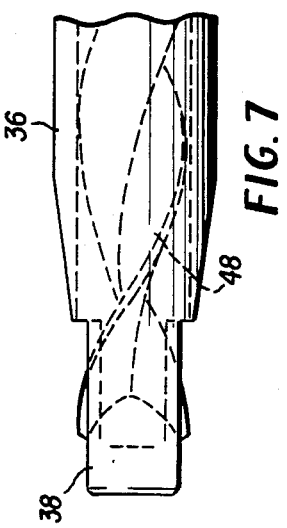
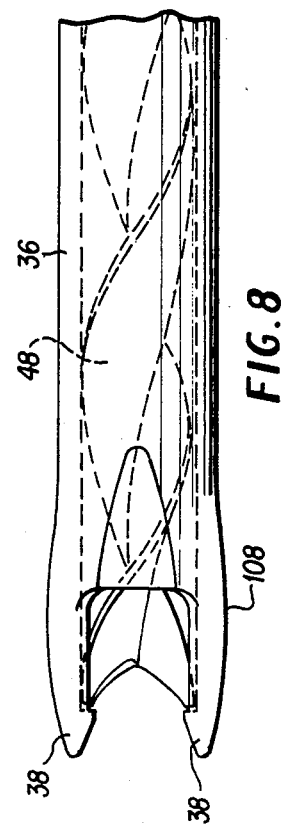
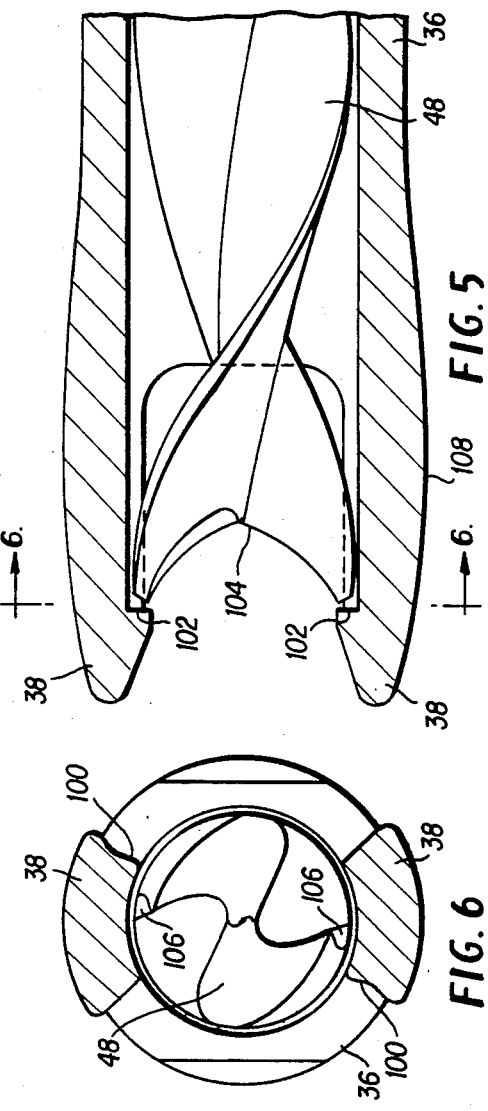
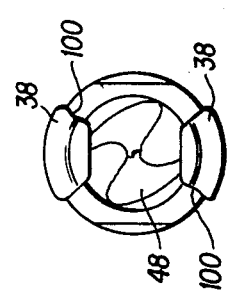

SURGICAL INSTRUMENT

This invention relates to a hand held surgical instrument for removing body tissue from a human body and, more particularly, to such a surgical instrument that is particularly useful in arthroscopic surgery.

BACKGROUND OF THE INVENTION

Heretofore it has been known to use coaxially mounted hollow tubes in the performance of arthroscopic knee surgery. Side cutting is effected by providing co-acting side edges of the tubes which diverge as cutting proceeds in the proximal direction. The outer tube is stationary and is provided with a side port which is opened and closed on each cycle by the inner rotating tube. Vacuum is used to remove the severed body tissue which is sequentially admitted through the port in the outer tube and then withdrawn through the inner tube. U.S. Pat. No. 4,203,444 to Bonnell et al and U.S. Pat. No. 4,274,414 to Johnson et al are examples of the previously described prior art.

These two patents are deficient in a number of respects. First of all, because the blades are made from tubular members, radial deflection is a critical problem. Bonnell et al acknowledges that even slight deflection, even on the order of one or two thousandths of an inch, of the rotating blade radially relative to the stationary blade can result in jamming of tissues cut from the knee. Secondly, neither of the devices in these two patents are useful in cutting straight ahead, i.e., to give an axial bore cut. Both patents are used for side cutting only. Thirdly, because of the manner in which tissue is introduced into the cutters in these patents, namely, by opening and closing a port in the side of a tube, the speed of cutting is much too slow. In U.S. Pat. No. 4,203,444 to Bonnell rotational speeds are limited to 200 rpm or below.

SUMMARY OF THE PRESENT INVENTION

In accordance with the present invention the aforementioned difficulties and shortcomings of the known prior art are effectively overcome in the practice of the present invention. In particular, an auger-like cutter blade is rotated within a stationary cylindrical sheath member which supports the cutter blade throughout its length. Both the auger-like cutter blade and the cylindrical sheath are made from stainless steel and deflection of one relative to the other is not a problem.

The cylindrical sheath member is provided with a pair of longitudinally extending, diametrically opposed tabs at its distal end. A cutting edge is provided on a longitudinally dinally extending edge of each of the tabs which co-acts with a helical cutting edge of the auger-like cutter blade to provide side cutting of body tissue insertable between the tabs. In addition, the auger-like blade is provided with a generally concave distal end ground to provide a generally fish-tailed appearance at its outer end terminating in two diametrically opposed sharp portions capable of effecting an axial boring cut.

Finally, the surgical instrument is designed for very rapid cutting speeds. In many applications, including arthroscopic knee surgery and arthroscopic shoulder surgery a rotational speed for the auger-like helical cutter blade of about 3,000 rpm is used. The surgical instrument of the present invention is adaptable to the skill of the operating surgeon. A lower speed of 1,000 rpm is possible while upper rotational speeds of 10,000 rpm or even higher are attainable for delicate operations such as an operation on the human eye.

The inherent advantages and improvements of the present invention will become more readily apparent by reference to the following detailed description of the invention and by reference to the drawings wherein:

FIG. 1 is a fragmentary perspective view illustrating the position of the surgical instrument of the present invention when used in arthroscopic surgery of a knee;

FIG. 2 is a plan view illustrating one form of a torn meniscus;

FIG. 3 is an exploded perspective view of the surgical instrument of FIG. 1;

FIG. 4 is a front elevational view taken partially in vertical cross section and with portions thereof removed of the surgical instrument of FIG. 1;

FIG. 5 is a fragmentary front elevational view taken partially in vertical cross section showing the cutting end of the surgical instrument of FIG. 4, but drawn to an enlarged scale;

FIG. 6 is an elevational view taken in vertical cross section along line 6—6 of FIG. 5;

FIG. 7 is a fragmentary top plan view of the surgical instrument of FIG. 5, but drawn to a reduced scale;

FIG. 8 is a fragmentary front elevational view of the surgical instrument shown in FIG. 7;

FIG. 9 is an end elevational view of the surgical instrument shown in FIG. 8;

DETAILED DESCRIPTION OF THE INVENTION

Referring now to FIG. 1 of the drawings, there is illustrated a surgical instrument indicated generally at 20 with the instrument being inserted into a small puncture site below the patella of the knee joint of a patient P. Not shown in the figure are conventional elements including another small puncture site to receive a fiber optic device to light the interior of the joint from a suitable light source which return a visual image either directly to an eye piece for the surgeon or preferably with recording cameras to a visual display which is observed by the surgeon in performing the operation. Also not specifically illustrated is the external introduction of a saline solution through another small puncture site at the knee.

A vacuum line hose 22 is illustrated attached to the surgical instrument and a pneumatic drive hose 24 drives a motor within motor assembly 78. Compressed nitrogen is usually used for this purpose. Alternatively, an electric motor can be used, although special precautions must be taken to ensure the safety of the patient, especially when saline solutions and the like are being employed.

Reference to FIG. 2 illustrates a meniscus indicated generally at 26. This meniscus is generally C-shaped in cross section and is illustrated to have a tear at 28. This is only one of a great many different configurations that a damaged meniscus may have. In order to prevent the damaged meniscus tissue from being pinched between the bones comprising the knee joint, extraneous tissue will be removed by making a cut substantially along the dashed lines 30, 32 in order to provide a relatively smooth configuration for the tissue at the site of the meniscus.

Figure 10:
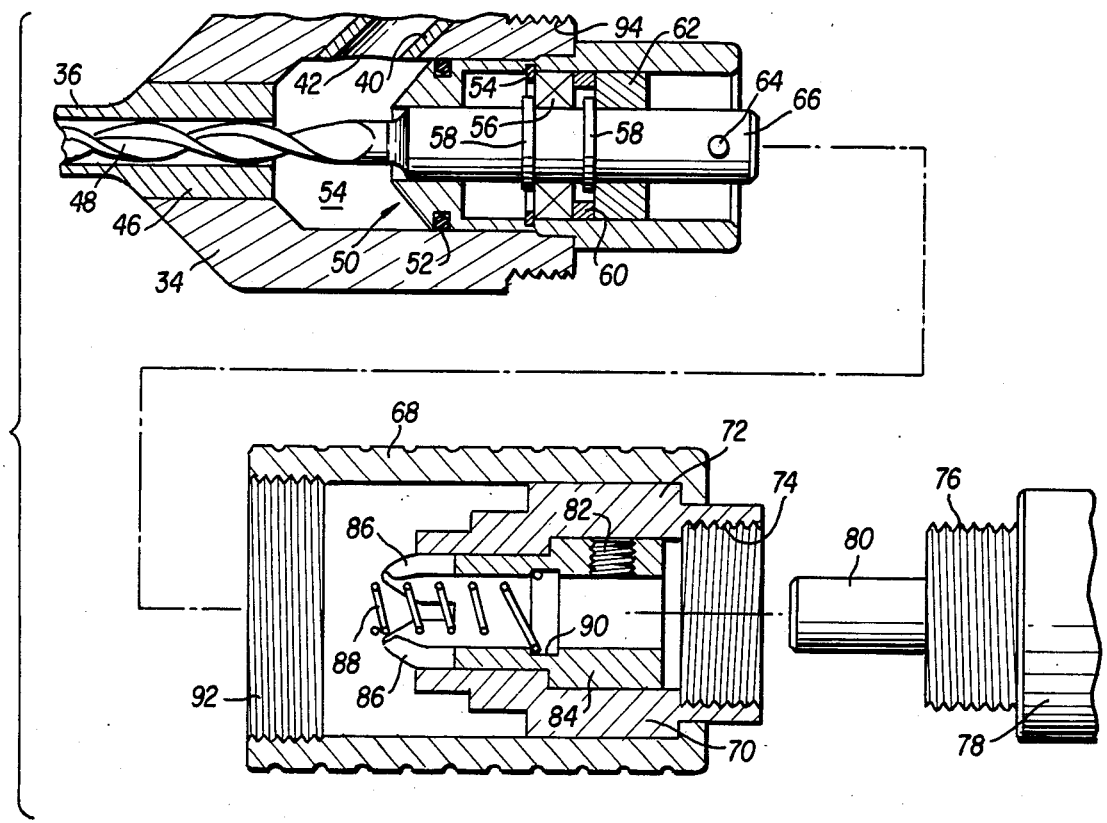
FIG. 10 is a fragmentary, exploded, elevational view, taken in vertical cross section illustrating the assembly of the major components of the surgical instrument of FIG. 1.
Figure 11:
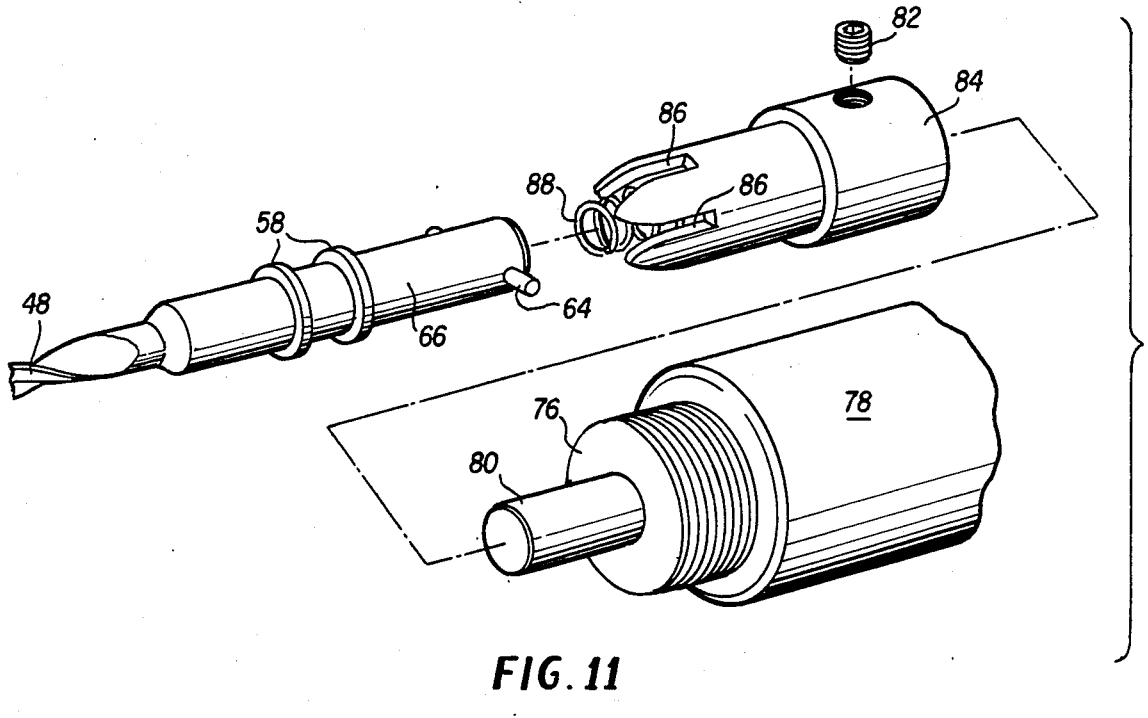
FIG. 11 is a fragmentary, exploded perspective view, with components removed illustrating further assembly operations for the surgical instrument of FIG. 1.

FIG. 3 illustrates in an exploded view, a number of the major elements of the surgical instrument. Thus, there is illustrated a suction housing member 34 which prior to being assembled is open at both ends as may be seen by an inspection of FIGS. 4 and 10. A cylindrical sheath member 36 is illustrated which is open at both ends and terminates at its distal end in a pair of longitudinally extending, diametrically opposed tabs 38. A vacuum tube 40 is secured to the suction housing member 34 at port 42 as seen in FIGS. 4 and 10. Vacuum tube 40 is provided with a series of hose barb seal members 44 in order to receive and retain the vacuum line hose 22.

As can be seen best in FIGS. 4 and 10, the cylindrical sheath member 36 is provided with a sealing head plug member 46 inserted into one open end of the suction housing member 34. An auger-like helical cutter blade 48 received and supported by cutter housing member indicated generally at 50 is inserted within the cylindrical sheath member and resides in closely spaced relationship thereto. FIGS. 4 and 10 also illustrate the use of an O-ring on the cutter housing member 50 so as to provide a seal with the interior of the suction housing member 34 on the side of port 42 that is remote from the cylindrical sheath member 36. A C-shaped spring retainer 54 forms a longitudinal stop for an internal bearing 56. The helical cutter 48 is provided with a thickened end shaft 66 having hub ring members 58 thereon which straddle the bearing 56. A spacer member 60 with any required shim members are used to obtain the proper longitudinal spacing for the distal end of helical cutter 48 with respect to the tab members 38. An end seal member 62 is then placed next to the spacer and/or shim members. An additional constructional feature of the cutter blade includes a pin drive member 64 diametrically inserted through the thickened end shaft 66.

A quick disconnect nut member 68 is carried or trapped on a cutter drive coupling nut member 70 by virtue of a raised boss 72 (FIG. 10) on the cutter drive coupling nut member 70. Left handed threads are provided at 74 on the cutter drive coupling nut member 70 and threaded on the exterior left hand threads 76 of motor assembly 78. A hose receptor 79 is provided for the motor assembly 78 at one end and the motor shaft 80 extends to the left at the other end in FIGS. 4 and 10. Screw 82 secures a cutter drive coupling member 84 to the shaft 80 of the motor. The cutter drive coupling member 84 is slotted at 86 and provided with a widely tapering end so as to self-seat the pin drive member 64 of the helical cutter blade 48. Spring 88 is retained within the cutter drive coupling member 84 by means of recess 90 in the cutter drive coupling member 84 and engages the end of the thickened end shaft 66 so as to urge the auger-like helical cutter blade 48 constantly toward its distal end eliminating any positional change caused by any backlash in the geared drive motor.

In order to effect a quick disconnect for the surgical instrument and to gain access to the cutting blade, the quick disconnect nut member 68 is provided with internal threads 92 engageable with external threads 94 of the suction housing member 34. By simply unscrewing this connection, the end of the cutter housing member 50, which is knurled at 95 as illustrated in FIG. 3, is simply pulled away from the cylindrical sheath member whereby any jammed tissue may be removed. Alternatively, a different size of helioal cutter 48 and cylindrical sheath 36 may be inserted.

Figure 12:
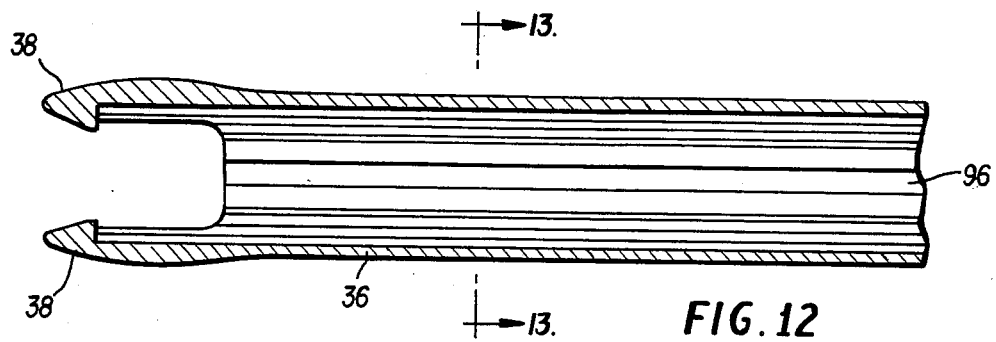
FIG. 12 is a fragmentary elevational view of a modified sheath member taken in vertical cross section.
Figure 13:
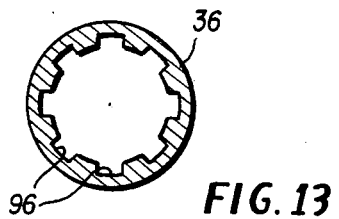
FIG. 13 is an elevational view taken in, vertical cross section along line 13—13 of FIG. 12.
Figure 14:
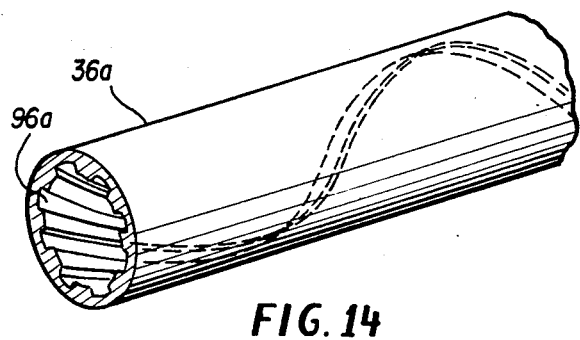
FIG. 14 is a fragmentary perspective of another modified sheath member with a vertical cross section cut.

Certain measures may be taken to minimize lodging of the tissue within the surgical instrument and these are shown in FIGS. 12–14 to include the application of straight grooves such as that shown in FIGS. 12 and 13 within the cylindrical sheath member 36 or the use of spiral grooves 96a within cylindrical sheath member 36a in FIG. 14. The direction of spiralling of the spiral grooves 96a is preferably opposite to that of the spiralling of the helix on the cutter blade 48.

Further details of the distal end of the auger-like helical cutting blade 48 and cylindrical sheath member 36 may be seen in FIGS. 5–9. In particular, one longitudinally extending edge of each of the tabs 38 is ground to provide a cutting edge 100. The edge of the helical spiral on the helical cutter blades 48 cooperate with these cutting edges 100 to provide lateral shearing of tissue which is inserted laterally between the tabs 38. The tabs 38 are undercut at 102 to provide a protective outer stop shoulder or lip for the blade 48. With the aid of spacer member 60 and any required shims, the outer edge of the cutter blade 48 is positioned from about two to about four thousandths of an inch away from the hook-like undercut portion of the tab members 38.

In addition, the auger-like helical cutting blade 48 is provided with a generally concave distal end at 104 that is ground to provide a generally fish-tailed appearance at its outer end terminating in two diametrically opposed sharp portions or types 106 so that the surgical instrument is capable of making what is called a plunge cut or an axial boring cut. To increase the stiffness of the surgical instrument, it is possible to provide increased thickness at the region of the tab members such as is shown at 108 in FIGS. 5 and 8.

It is possible to vary the details of the blade cutter to suit the skill of the surgeon as well as to vary it to accommodate different tissues that are inserted between the tab members 38. For example, the back angle or sharp edge at 106 on the helical cutter blade 48 may be varied from about 35 degrees minimum to an angle approaching 90 degrees. If this angle is too blunt, no cutting will be effected and if it is too steep, the cutting edge becomes fragile. It is also possible to vary the width of the tab members 38 of the sheath. As the width is made narrower, it is possible to cut faster. This width may be either less than the diameter of the blade or greater than the diameter of the blade. Once again the width is varied dependent upon the skill of the surgeon.

As far as the amount of suction is concerned, 27 inches of mercury is deemed to be high suction and will work very satisfactorily with the surgical instrument of the present invention. Twelve to 16 inches of mercury is considered to be marginal and if the suction is less than that, the chances of clogging the spiral groove in the auger-like helical cutter blade 48 becomes much greater. The auger-like blade with its helical groove serves as a conduit for severed tissue under the influence of the vacuum connected to vacuum tube 40.

While presently preferred embodiments of the invention have been illustrated and described, it will be recognized that the invention may be otherwise variously embodied and practiced within the scope of the claims which follow.

We claim:

1. In a hand held surgical instrument of the type used to perform closed surgery such as arthroscopic surgery of the kneee wherein a motor drive is used to rotate a cutter blade within a stationary outer cylindrical sheath member and vacuum pressure is used to remove the severed tissue, the improvement which comprises
   a. a helical cutter blade extending within said cylindrical sheath member in closely spaced relationship,
   b. said cylindrical sheath member having a longitudinal axis and being substantially completely open at both ends and terminating at its distal end in a pair of longitudinally extending diametrically opposed tabs, each tab terminating in a radially inwardly extending lip, said lips being slightly spaced from the distal end of said helical cutter blade,
      (1) one longitudinally extending edge of each of said tabs being ground to provide a cutting edge,
      (2) said helical cutter blade cooperating with said cutting edge on each of said tabs to sever tissue inserted laterally between said tabs in a scissor-like cut upon rotation of said helical cutter blade,
      (3) said helical cutter blade further having at least a portion of its distal end ground to provide a concave distal end providing a generally fish tailed appearance terminating in two diametrically opposed sharp tynes so that the instrument is capable of making an axial boring cut and wherein the length of the concavity of said concave distal end in a direction along the longitudinal axis of said cylindrical sheath is less than the length of said tabs.

2. A hand held surgical instrument as defined in claim 1 wherein the grinding of said helical cutter to produce two diametrically opposed sharp portions to produce axial boring cuts forms an angle of at least 35 degrees with an axis parallel to the longitudinal axis of said helical cutter.

3. A hand held surgical instrument as defined in claim 1 wherein said cylindrical sheath is internally grooved to assist in the removal of severed tissue.

4. A hand held surgical instrument as defined in claim 1 wherein the distal end of said sheath is thickened.

5. A hand held surgical instrument as defined in claim 1, wherein said motor drive rotates said cutter blade at a rotational speed of at least 1000 rpm.

6. In a hand held surgical instrument of the type used in closed surgery such as arthroscopic surgery of the knee wherein a motor drive is used to rotate a cutter blade within a stationary outer cylindrical sheath member and vacuum pressure is used to remove severed tissue, the improvement which comprises
   a. a helical cutter blade extending within said cylindrical sheath member in closely spaced relationship to guide severed tissue under the influence of said vacuum pressure to remove said severed tissue from said surgical instrument,
   b. said cylindrical sheath member having a longitudinal axis and being substantially completely open at both ends and terminating at its distal end in a pair of longitudinally extending diameterically opposed tabs,
      (1) one longitudinally extending edge of each of said tabs being ground to provide a cutting edge,
      (2) said helical cutter blade cooperationg with said cutting edge on each of said tabs to sever tissue inserted laterally between said tabs in a scissor-like cut upon rotation of said helical cutter blade,
      (3) said helical cutter blade further having at least a portion of its distal end ground to provide a concave distal end providing a generally fish tailed appearance terminating in two diametrically opposed sharp tynes, each of said tynes presenting a generally radially extending cutting edge so that the instrument is also capable of making an axial boring cut independently of said external tabs and wherein the length of the concavity of said concave distal end in a direction along the longitudinal axis of said cylindrical sheath is less than the length of said tabs.

* * * * *